US008524955B2

(12) United States Patent
Poss et al.

(10) Patent No.: US 8,524,955 B2
(45) Date of Patent: Sep. 3, 2013

(54) PROCESS FOR THE PREPARATION OF HEXAFLUORO-2-BUTYNE

(75) Inventors: Andrew Joseph Poss, Kenmore, NY (US); David Nalewajek, West Seneca, NY (US); Haridasan K. Nair, Williamsville, NY (US); Michael Van Der Puy, Amherst, NY (US); Rajiv Ratna Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 319 days.

(21) Appl. No.: 13/110,974

(22) Filed: May 19, 2011

(65) Prior Publication Data

US 2011/0288348 A1 Nov. 24, 2011

Related U.S. Application Data

(60) Provisional application No. 61/347,150, filed on May 21, 2010.

(51) Int. Cl.
*C07C 17/093* (2006.01)

(52) U.S. Cl.
USPC ............ 570/155; 570/156; 570/153; 570/163

(58) Field of Classification Search
USPC ................................. 570/156, 153, 163, 155
See application file for complete search history.

(56) References Cited

U.S. PATENT DOCUMENTS

| 4,734,503 | A | * | 3/1988 | Weigert | 546/345 |
| 4,814,522 | A | * | 3/1989 | Weigert | 570/160 |
| 5,210,340 | A | | 5/1993 | Bielefeldt et al. | |
| 6,479,717 | B1 | * | 11/2002 | Cuzzato et al. | 570/163 |
| 7,109,386 | B2 | * | 9/2006 | Mathieu | 570/161 |
| 2008/0269532 | A1 | | 10/2008 | Swearingen | |
| 2009/0012335 | A1 | * | 1/2009 | Nappa et al. | 570/153 |
| 2009/0156869 | A1 | * | 6/2009 | Nappa | 570/156 |

FOREIGN PATENT DOCUMENTS

| EP | 2003109 A1 | 12/2008 |
| WO | 2010014548 A2 | 2/2010 |

OTHER PUBLICATIONS

Angelini, G., et al., Synthesis and tritium-induced fluorine-19 NMR shifts of 1,1,1,4,4,4-hexafluoro-2,3-ditritio-2-butene, Canadian Journal of Chemistry, 1992, pp. 1221-1228, vol. 70, No. 4, Ist. Chim. Nucl., CNR, Rome, Italy.

* cited by examiner

*Primary Examiner* — Johann R Richter
*Assistant Examiner* — Pancham Bakshi
(74) *Attorney, Agent, or Firm* — Bruce O. Bradford

(57) ABSTRACT

Disclosed is a process for making hexafluoro-2-butyne comprising the steps of: (a) providing a composition comprising $CF_3CX=CXCF_3$, where X=halogen; and (b) treating $CF_3CX=CXCF_3$ with a dehalogenation catalyst in the presence of a halogen acceptor compound Y, where Y is not hydrogen. The halogen acceptor compound Y is a material capable of being halogenated, preferably a compound having a multiple bond, such as an alkyne, alkene, allene, or carbon monoxide. Another suitable material capable of being halogenated is a cyclopropane. A catalyst effectively transfers halogen from $CF_3CX=CXCF_3$ to the halogen acceptor compound. Since Y is not hydrogen, the formation of $CF_3CX=CHCF_3$ is greatly reduced or eliminated.

15 Claims, No Drawings

PROCESS FOR THE PREPARATION OF HEXAFLUORO-2-BUTYNE

CROSS-REFERENCE TO RELATED APPLICATION

This application claims domestic priority from commonly owned, copending, U.S. Provisional Patent Application Ser. No. 61/347,150, filed 21 May 2010, the disclosure of which is hereby incorporated herein by reference.

FIELD OF THE INVENTION

The present disclosure relates to a process for the preparation of a perfluorinated alkyne, and more specifically the preparation of 1,1,1,4,4,4-hexafluoro-2-butyne:

$$CF_3-C\equiv C-CF_3.$$

BACKGROUND OF THE INVENTION

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials (GWP) associated therewith, it is desirable to use fluids having the lowest possible greenhouse warming potential in addition to zero ozone depletion potential (ODP). Thus there is considerable interest in developing environmentally friendlier materials for the applications mentioned above.

Fluorinated butenes having zero ozone depletion and low global warming potential have been identified as potentially filling this need. However, the toxicity, boiling point, and other physical properties in this class of chemicals vary greatly from isomer to isomer. One fluorobutene having valuable properties is cis-1,1,1,4,4,4-hexafluorobutene. Thus, there is a need for new manufacturing processes for the production of hexafluorobutenes and in particular cis-1,1,1,4,4,4-hexafluorobutene:

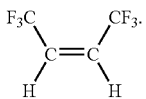

A key synthetic precursor to this material is the known compound 1,1,1,4,4,4-hexafluoro-2-butyne.

Hexafluoro-2-butyne has been made by the dechlorination of $CF_3CCl\!=\!CClCF_3$ with zinc in ethanol (J. Am. Chem. Soc., 71 (1949) 298). This process generates zinc salts and co-produces substantial amounts of $CF_3CH\!=\!CClCF_3$ as well.

U.S. Patent Publication No. 2009/0156869 describes the catalytic dehalogenation of $CF_3CCl\!=\!CFCF_3$ which gives the desired butyne along with substantial amounts of the hydrodechlorination product, $CF_3CH\!=\!CFCF_3$.

Thus there is a need to produce the desired alkyne from a suitable precursor in such a way that the formation of substantial amounts of hydrodechlorination by-products (e.g., $CF_3CH\!=\!CXCF_3$) is avoided.

SUMMARY OF THE INVENTION

One embodiment of the present invention is thus directed to a process for making hexafluoro-2-butyne comprising the steps of:

(a) providing a composition comprising $CF_3CX\!=\!CXCF_3$, where X=halogen; and (b) treating $CF_3CX\!=\!CXCF_3$ with a dehalogenation catalyst in the presence of a halogen acceptor compound Y, where Y is not hydrogen.

In certain embodiments of the reaction described above, the halogen X is chlorine. In certain embodiments of the reaction, the halogen acceptor compound Y comprises a material with at least one multiple bond. One preferred multiple bond compound comprises an alkyne compound. Another preferred multiple bond compound comprises an alkene compound. Yet another preferred multiple bond compound comprises an allene compound. Another preferred multiple bond compound comprises carbon monoxide. In certain embodiments of the reaction the halogen acceptor compound Y comprises a cyclopropane compound.

In certain embodiments of the reaction described above, the catalyst comprises a material capable of transferring chlorine from one molecule to another. One preferred catalyst comprises a dehalogenation catalyst. Another preferred catalyst comprises an oxychlorination catalyst. In certain embodiments the catalyst further comprises a catalyst modifier or promoter. In certain embodiments the catalyst further comprises a catalyst support.

Another embodiment of the present invention extends the process described above by the additional step of converting the product alkyne compound to cis-hexafluoro-2-butene. Preferably the conversion is a catalytic reduction or a chemical reduction with boranes, or the like.

DETAILED DESCRIPTION OF THE INVENTION

As set forth above, one embodiment of the present invention is a process for making hexafluoro-2-butyne, comprising the steps of:

(a) providing a composition comprising $CF_3CX\!=\!CXCF_3$, where X=halogen; and (b) treating the $CF_3CX\!=\!CXCF_3$ with a dehalogenation catalyst in the presence of a halogen acceptor compound Y, where Y is not hydrogen.

In this process, the halogen X is preferably chlorine. The halogen acceptor compound Y is a material capable of being halogenated, preferably a compound having one or more multiple bonds, i.e., double and/or triple bonds. Such compounds include alkynes, alkenes, allenes, and carbon monoxide. Another suitable material capable of being halogenated is a cyclopropane.

A catalyst effectively transfers halogen from $CF_3CX\!=\!CXCF_3$ to the halogen acceptor compound. Since Y is not hydrogen, the formation of $CF_3CX\!=\!CHCF_3$ is greatly reduced or eliminated.

In a preferred embodiment the generalized reaction is:

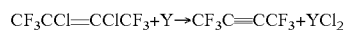

In another preferred embodiment, the reaction is:

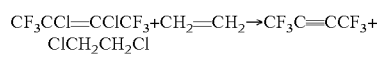

In yet another preferred embodiment the reaction is:

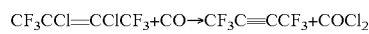

In general the catalyst can be any material capable of transferring chlorine from one molecule to another. These materials may be known as dehalogenation catalysts in the art. Preferred catalysts are those which may be known as oxychlorination catalysts in the art. Such catalysts include copper and its salts, in particular $CuCl_2$.

Catalyst modifiers or promoters may also be used, which include alkali metal salts such as sodium, potassium, or cesium chloride, with potassium chloride being preferred among them. Support materials include silica, calcium fluoride, alumina, titanium oxide, and combinations thereof.

The catalyst may also be comprised of combinations of metals such as copper with nickel or chromium and combinations of metal halides such as $CuCl_2$ with $LaCl_3$. The catalyst materials may also be comprised of KCl on silica, $MgCl_2$, or precious metals such as palladium. When acetylenes are used they should have an internal C≡C bond (e.g., 2-butyne) if the catalyst is capable of catalyzing the dimerization of terminal alkynes.

The reactions are preferably carried out in the gas phase where reaction temperatures are in the range of 200° C. to 350° C. range, depending on the catalyst used, with more typical temperatures ranging from about 250° C. to 300° C. Pressures may be atmospheric or greater than atmospheric, up to about 10 atmospheres.

The effluent from the reactor from the reaction using $CF_3CCl=CClCF_3$ consists of product $CF_3C\equiv CCF_3$, by-product $YCl_2$, and unreacted starting materials. Choice of the best Y molecule is in part dictated by the boiling points of the starting material and by-products so that the components in the product stream are readily separated by distillation. Thus $CF_3Cl=CClCF_3$ (bp 68° C. to 69° C.) could be used with Y=ethylene (bp −104° C.) leading to hexafluoro-2-butyne (bp −25° C.) and 1,2 dichloroethane (bp 83° C.) or with Y=carbon monoxide (bp −191° C.) leading to by-product $COCl_2$ (bp 8° C.).

As described above, the process of the present invention can be extended to include step (c) in which the hexafluoro-2-butyne compound is reduced to cis-hexafluoro-2-butene. This can be accomplished by catalytic reduction over a Lindlar catalyst or with certain chemical reducing agents, such as borane and di-sec-amylborane.

The following examples are provided to further illustrate the invention and should not be taken as limitations of the invention.

EXAMPLE 1

A catalyst comprised of 5 wt % $CuCl_2$ and 3 wt % KCl on alumina pellets is the catalyst for this example. A vaporized 1:1.2 mixture of $CF_3Cl=CClCF_3$ and 2-butyne is passed over 15 cc of the dried catalyst at 275° C. at a combined flow rate of 25 cc/min. The effluent gases are analyzed by gas chromatography. The analysis shows the presence of both $CF_3C\equiv CCF_3$ and 2,3-dichloro-2-butene.

EXAMPLE 2

Example 1 is repeated using a catalyst comprised of 22 wt % $CuCl_2$ and 5 wt % KCl on silica. The reaction temperature is 300° C. and the halogen acceptor is carbon monoxide (1:1 molar ratio). An analysis of the effluent stream shows the presence of both $CF_3C\equiv CCF_3$ and phosgene.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process for making hexafluoro-2-butyne comprising the steps of:
   (a) providing a composition comprising $CF_3CX=CXCF_3$, where X=halogen; and
   (b) treating $CF_3CX=CXCF_3$ with a dehalogenation catalyst in the presence of a halogen acceptor compound Y, where Y is alkyne, alkene, allene, carbon monoxide or cyclopropane.

2. The process of claim 1, wherein the halogen X is chlorine.

3. The process of claim 1, wherein the halogen acceptor compound Y is an alkyne compound.

4. The process of claim 1, wherein the halogen acceptor compound Y is an alkene compound.

5. The process of claim 1, wherein the halogen acceptor compound Y is an allene compound.

6. The process of claim 1, wherein the halogen acceptor compound Y is carbon monoxide.

7. The process of claim 1, wherein the halogen acceptor compound Y is a cyclopropane compound.

8. The process of claim 1, wherein the catalyst comprises a material capable of transferring chlorine from one molecule to another.

9. The process of claim 8, wherein the catalyst comprises a dehalogenation catalyst.

10. The process of claim 8, wherein the catalyst comprises an oxychlorination catalyst.

11. The process of claim 8, wherein the catalyst further comprises a catalyst modifier or promoter.

12. The process of claim 8, wherein the catalyst further comprises a catalyst support.

13. The process of claim 1, further comprising step (c) in which the product alkyne is further converted to cis-hexafluoro-2-butene.

14. The process of claim 13, wherein the conversion is a catalytic reduction with a Lindlar catalyst.

15. The process of claim 13, wherein the conversion is a chemical reduction with a borane compound.

* * * * *